US007053064B2

(12) United States Patent
Lukas

(10) Patent No.: US 7,053,064 B2
(45) Date of Patent: May 30, 2006

(54) COMPOUNDS FOR THE TREATMENT OF TOBACCO DEPENDENCE AND WITHDRAWAL

(75) Inventor: Scott Lukas, Boxboro, MA (US)

(73) Assignee: The McLean Hospital Corporation, Boston, MA (US)

( * ) Notice: Subject to any disclaimer, the term of this patent is extended or adjusted under 35 U.S.C. 154(b) by 0 days.

(21) Appl. No.: 10/703,695

(22) Filed: Nov. 6, 2003

(65) Prior Publication Data
US 2004/0167093 A1 Aug. 26, 2004

Related U.S. Application Data

(60) Provisional application No. 60/424,972, filed on Nov. 8, 2002.

(51) Int. Cl.
A01N 43/04 (2006.01)
A61K 31/70 (2006.01)

(52) U.S. Cl. .............................. 514/51; 514/45; 514/46; 514/47; 514/48; 514/49

(58) Field of Classification Search .................. 514/45, 514/46, 47, 48, 49, 51
See application file for complete search history.

(56) References Cited

U.S. PATENT DOCUMENTS

| 4,027,017 | A | | 5/1977 | Hata et al. |
| 4,048,316 | A | | 9/1977 | Penn |
| 4,115,576 | A | | 9/1978 | Penn |
| 4,704,361 | A | | 11/1987 | Miccoli et al. |
| 4,999,382 | A | | 3/1991 | Wurtman |
| 5,179,126 | A | | 1/1993 | Wurtman |
| 5,278,176 | A | | 1/1994 | Lin |
| 5,409,946 | A | | 4/1995 | Garvey et al. |
| 5,472,958 | A | | 12/1995 | Gunn, Jr. et al. |
| 5,691,320 | A | | 11/1997 | von Borstel et al. |
| 5,691,365 | A | * | 11/1997 | Crooks et al. .............. 514/343 |
| 5,919,789 | A | | 7/1999 | Dyke et al. |
| 5,958,896 | A | * | 9/1999 | Renshaw et al. ............. 514/49 |
| 5,977,174 | A | | 11/1999 | Bradley et al. |
| 6,103,703 | A | * | 8/2000 | Renshaw et al. ............. 514/49 |
| 6,153,653 | A | | 11/2000 | Shashoua |
| 6,277,855 | B1 | * | 8/2001 | Yerxa ........................ 514/256 |
| 2002/0019364 | A1 | | 2/2002 | Renshaw |
| 2002/0182196 | A1 | | 12/2002 | McCleary |
| 2003/0114415 | A1 | | 6/2003 | Wurtman et al. |
| 2003/0220291 | A1 | | 11/2003 | Renshaw |
| 2004/0176316 | A1 | | 9/2004 | Renshaw et al. |

FOREIGN PATENT DOCUMENTS

| DE | 3400276 A1 | 7/1985 |
| EP | 0 188647 A1 | 7/1986 |
| EP | 0218190 A2 | 4/1987 |
| EP | 0218190 B1 | 11/1989 |
| JP | 63-202854 | 8/1988 |
| JP | 08183737 | 7/1996 |
| WO | WO 99/26620 | 6/1999 |
| WO | WO 00/06174 | 2/2000 |
| WO | WO 01/72288 A2 | 10/2001 |

OTHER PUBLICATIONS

Grau et al. Arzneimittel-Forschung (1983), vol. 33 (7A), pp. 1025-1026.*
Agnoli, et al., "Efficacy of CDP choline in Chronic Cerebral Vascular Diseases (CCVD)," *Novel Biochemical, Pharmacological and Clinical Aspects of Cytidinediphosphocholine* Elsevier (1985) 305-315.
Babb, et al., "Differential Effect of CDP-clholine on Brain Cytosolic Choline Levels in Younger and Older Subjects as Measured by Proton Magnetic Resonance Spectroscopy," *Psychopharmacology* (1996) 127:88-94.
Boudouresques, et al., "Therapeutic Conduct in Light of a Cerebral Vascular Accident and the Use of CDP-choline," *International Symposium: Brain Suffering and Precursors of Phospholipids* pp. 1-13 (1980).
Brown et al., "CNS Complications of Cocaine Abuse: Prevalence, Pathophysiology, and Neuroradiology," *Am. J. Roentgenol.* (1992) 159:137-147.
Centrone et al., "Use of Citicoline in High Dosages in Acute Cerebrovascular Disease," *Minerva Med.* (1986) 77:371-373 (English Abstract).
Chang et al., "Neurochemical Alterations in Asymptomatic Abstinent Cocaine Users: A Proton Magnetic Resonance Spectroscopy Study," *Biol. Psychiatry* (1997) 42:1105-1114.
Christensen et al., "Abnormal Cerebral Metabolism in Polydrug Abusers During Early Withdrawal: A $^{31}$P MR Spectroscopy Study," *Magn. Reson. Med.* (1996) 35:658-663.
Citicoline Sodium (CDP-Choline), *Investigator's Brochure*, Revised: Apr. 1994 by Interneuron Pharmaceuticals, Inc.
Cohen et al., "Decreased Brain Choline Uptake in Older Adults," *JAMA* (1995) 274:902-907.
English et al., "Elevated Frontal Lobe Cytosolic Choline Levels in Minimal or Mild AIDS Dementia Complex Patients: A Proton Magnetic Resonance Spectroscopy Study," *Biol. Psychiatry* (1997) 41:500-502.
Gallai et al., "Study of the P300 and Cerebral Maps in Subjects with Multi-Infarct Dementia Treated with Cytidine," *Psychopharmacology* (1991) 103:1-5.
Galletti et al., "Biochemical Rationale for the Use of CDP-choline in Traumatic Brain Injury: Pharmacokinetics of the Orally Administered Drug," *J. Neurol. Sci.* (1991) 103:S19-S25.

(Continued)

*Primary Examiner*—Patrick Lewis
(74) *Attorney, Agent, or Firm*—Clark & Elbing LLP

(57) ABSTRACT

The invention provides methods for treating or suppressing tobacco or nicotine usage or dependence involving administration of a therapeutically-effective amount of a cytosine-containing or cytidine-containing compound, creatine-containing compound, adenosine-containing, or adenosine-elevating compound to a mammal.

6 Claims, 2 Drawing Sheets

OTHER PUBLICATIONS

Hoff et al., "Effects of Crack Cocaine on Neurocognitive Function," *Psychiatry Res.* (1996) 60:167-176.

Jacobs et al., "Cocaine Abuse: Neurovascular Complications," *Radiology* (1989)170:223-227.

Kaufman et al., "Cocaine-Induced Cerebral Vasoconstriction Detected in Humans with Magnetic Resonance Angiography," *JAMA* (1998) 279:376-380.

Kreek "Opiate and Cocaine Addictions: Challenge for Pharmacotherapies," *Pharmacol. Biochem. Behav.* (1997) 57:551-569.

Levin et al., "Improved Regional Cerebral Blood Flow in Chronic Cocaine Polydrug Users Treated with Buprenorphine," *J. Nucl. Med.* (1995) 36:1211-1215.

London et al., "Cerebral Glucose Utilization in Human Heroin Addicts: Case Reports from a Positron Emission Tomographic Study," *Res. Commun. Subst. Abuse* (1989) 10:141-144.

Lukacsko et al., "Modulation of the Vasoconstrictor Response to Adrenergic Stimulation by Nucleosides and Nucleotides," *J. Pharmacol. Exp. Ther.* (1982) 222:344-349.

Lukas et al., "Effects of Short-term Citicoline Treatment on Acute Cocaine Intoxication and Cardiovascular Effects," *Psychopharmacology* (2001) 157:163-7.

Maas et al., "Functional Magnetic Resonance Imaging of Human Brain Activation During Cue-induced Cocaine Craving," *Am. J. Psychiatry* (1998) 155:124-126.

Malec et al., "Influence of Adenosinergic Drugs on Ethanol Withdrawal Syndrome in Rats," *Pol. J. Pharmacol.* (1996) 48:583-588.

McCance, "Overview of Potential Treatment Medications for Cocaine Dependence," *NIDA Res. Monogr.*, (1997) 175:36-72.

Moglia et al., "Citicoline in Patients with Chronic Cerebrovascular Diseases (CCVD): Quantitative EEG Study," *Curr. Ther. Res.* (1984) 36:309-313.

Monticone et al., "On the Therapeutic Use of Nucleosides, Cytidine and Uridine, in some Neurological Diseases," *Minerva Med.* (1966) 57:4348-52.

O'Rourke et al., "Effect of Chronic Cocaine Exposure on Carotid Artery Reactivity in Neonatal Rabbits," *Life Sci.* (1996) 59:119-130.

Page, et al., "Developmental Disorder Associated with Increased Cellular Nucleotidase Activity," *Proc. Natl. Acad. Sci. USA* (1997) 94:11601-11606.

Peterson et al., "Neurovascular Complications of Cocaine Abuse," *J. Neuropsychiatry Clin. Neurosci.*, (1991) 3:143-149.

Renshaw et al., "Short-term Treatment with Citicoline (CDP)-choline) Attenuates Some Measures of Craving in Cocaine-Dependent Subjects: A Preliminary Report," *Psychopharmacology* (1999) 142:132-8.

Saligaut et al., "Circling Behaviour in Rats with Unilateral Lesions of the Nigrostriatum Induced by 6-Hydroxydopamine: Changes Induced by Oral Administration of Cytidine-5'-Diphosphocholine," *Neuropharmacology* (1987) 26:1315-1319.

Salvadorini et al., "Clinical Evaluation of CDP-choline (NICHOLIN®): Efficacy as Antidepressant Treatment," *Curr. Ther. Res.* (1975) 18:513-520.

Secades et al., "CDP-choline: Pharmacological and Clinical Review," *Meth. Find. Exp. Clin. Pharmacol.* (1995) 17(Suppl. B):1-54.

Self, et al., "Opposite Modulation of Cocaine-seeking Behavior by $D_1$- and $D_2$-like Dopamine Receptor Agonists," *Science* (1996) 271:1586-1589.

Shekim et al., "S-Adenosyl-L-Methionine (SAM) in Adults with ADHD, RS: Preliminary Results from an Open Trial," *Psychopharmacol. Bull.* (1990) 26:249-253.

Sholar et al., "Concurrent Pharmacokinetic Analysis of Plasma Cocaine and Adrenocorticotropic Hormone in Men," *J. Clin. Endocrinol. Metab.* (1998) 83:966-968.

Tazaki et al., "Treatment of Acute Cerebral Infarction with a Choline Precursor in a Multicenter Double-Blind Placebo-Controlled Study," *Stroke* (1988) 19:211-216.

Teoh et al., "Acute Interactions of Buprenorphine with Intravenous Cocaine and Morphine: An Investigational New Drug Phase I Safety Evaluation," *J. Clin. Psychopharmacol.* (1993) 13:87-99.

Tornos et al., "Effect of Oral CDP-Choline on Experimental Withdrawal Syndrome," *Arzneim.-Forsch./Drug Res.* (1983) 33:1018-1021.

Warner et al., "Pharmacotherapy for Opioid and Cocaine Abuse," *Med. Clin. North Am.* (1997) 81:909-925.

Weiss, "Metabolism and Actions of CDP-Choline as an Endogenous Compound and Administered Exogenously as Citicoline," *Life Sci.* (1995) 56:637-660.

Wurtman et al., "Effect of Oral CDP-choline on Plasma Choline and Uridine Levels in Humans," *Biochem. Pharmacol.* (2000) 60:989-992.

Alvarez et al., "Double-Blind Placebo-Controlled Study with Citicoline in APOE Genotyped Alzheimer's Disease Patients. Effects on Cognitive Performance, Brain Bioelectrical Activity and Cerebral Perfusion," *Methods Find Exp. Clin. Pharmacol.* (Abstract) 21:633-644 (1999).

Cartezon et al., "Antidepressant-Like Effects of Cytidine in the Forced Swim Test in Rats," *Biol. Psychiatry* 51:882-889 (2002).

Fernandez, "Efficacy and Safety of Oral CDP-Choline: Drug Surveillance Study in 2817 Cases," *Arzneimittelforschung. Drug Res.* 33:1073-1080 (1983).

Fioravanti et al., "Cytidinediphosphocholine (CDP Choline) for Cognitive and Behavioural Disturbances Associated with Chronic Cerebral Disorders in the Elderly," *Cochrane Database Systems* (Abstract) 2:CD000269 (2005).

Greenwell, "Enhancing Cognitive Function: Keeping Your Memory in Tip Top Shape," *LE (Life Extension) Magzine* (2000).

Katzung, "Basic & Clinical Pharmacology," *Appleton & Lang, Seventh Edition* pp. 62, and 521-523 (1998).

Pleul et al., "Lithium Therapy and the Turnover of Phosphatidylcholine in Human Erythrocytes," *Euro. J. Clin. Pharmacol.* 31:457-462 (1986).

Radulovacki, "Adenosine Analogs and Sleep in Rats," *J. Pharmacol. Exper. Ther.* 228:268-274 (1984).

Satoh et al., "Involvement of Adenosine $A_{2A}$ Receptor in Sleep Promotion," *Euro. J. Pharmacol.* 351:155-162 (1998).

Scammell et al., "An Adenosine A2a Agonist Increases Sleep and Induces Fos in Ventrolateral Preoptic Neurons," *Neurosci.* 107:653-663 (2001).

Shargel et al., "Comprehensive Pharmacy Review," *Lippincott Williams & Wilkins, Fourth Edition* 547-548 (2001).

Stoll et al., "Choline in the Treatment of Rapid-Cycling Bipolar Disorder: Clinical and Neurochemical Findings in Lithium-Treated Patients," *Biol. Psychiatry* 40:382-388 (1996).

* cited by examiner

COMPOUNDS FOR THE TREATMENT OF TOBACCO DEPENDENCE AND WITHDRAWAL

CROSS-REFERENCE TO RELATED APPLICATIONS

This application claims benefit of U.S. Provisional Application No. 60/424,972, file Nov. 8, 2002, hereby incorporated by reference.

BACKGROUND OF THE INVENTION

This invention relates to methods for the treatment or suppression of tobacco or nicotine dependence or usage.

Substance abuse disorders present unique complications for patients, clinicians, and care givers. These disorders are difficult to diagnose unequivocally and fear of societal condemnation, as well as lack of simple and effective therapies, often results in patients who are reluctant to disclose their symptoms to health professionals, leading to adverse societal and health consequences. Substance abuse disorders, e.g., tobacco or nicotine usage or dependence, occur in people of all ages and backgrounds.

Use of substances such as tobacco or nicotine often leads to addiction and dependence on these substances, causing a variety of adverse consequences, including clinical toxicity, tissue damage, physical dependence and withdrawal symptoms, and an impaired ability to maintain social and professional relationships. The etiology of substance abuse or dependence is unknown, although factors such as the user's physical characteristics (e.g., genetic predisposition, age, weight), personality, or socioeconomic class have been postulated to be determinants.

Simple and effective pharmacological treatments for these disorders have proven scarce to date. It would be beneficial to provide pharmacotherapies suitable for administration to all populations, including the elderly and children, for the treatment of tobacco or nicotine dependence or usage.

SUMMARY OF THE INVENTION

In general, the invention features methods of treating or suppressing tobacco or nicotine dependence or usage by administering a therapeutically-effective amount of a cytidine-containing, cytosine-containing, creatine-containing, uridine-containing, adenosine-containing, or adenosine-elevating compound to a mammal. Any of the cytidine-containing, cytosine-containing, creatine-containing, uridine-containing, adenosine-containing, or adenosine-elevating compounds of the invention may be administered separately.

In preferred embodiments, the cytidine-containing compound is cytidine, CDP, or CDP-choline; the cytidine-containing compound includes choline; and the mammal is a human child, adolescent, adult, or older adult. In other preferred embodiments, the CDP-choline is administered orally and the administration is chronic, e.g., treatment occurring over a period of greater than 1, 2, 3, 4, 5, 6, 7, 14, 21, 30, 60, 90, or 180 days or even over a period of greater than one year.

In other preferred embodiments, a brain phospholipid (e.g., lecithin) or a brain phospholipid precursor (e.g., a fatty acid or a lipid), is also administered to the mammal. In other preferred embodiments, an antidepressant is also administered to the mammal.

By use of "tobacco" is meant use of any form of tobacco including cigarettes, cigars, and smokeless tobacco.

By "abuse" is meant excessive use of a substance, particularly one that may modify body functions.

By "dependence" or "dependency" is meant any form of behavior that indicates an altered or reduced ability to make decisions resulting, at least in part, from the use of tobacco or nicotine. Representative forms of dependency behavior may take the form of antisocial, or inappropriate behavior and include those behaviors directed at the desire, planning, acquiring, and use of tobacco or nicotine. This term also includes the psychic craving for tobacco or nicotine that may or may not be accompanied by a physiological dependency, as well as a state in which there is a compulsion to use tobacco or nicotine, either continuously or periodically, in order to experience its psychic effects or to avoid the discomfort of its absence. Forms of dependency include habituation, that is, an emotional or psychological dependence on tobacco or nicotine to obtain relief from tension and emotional discomfort; tolerance, that is, the progressive need for increasing doses to achieve and sustain a desired effect; addiction, that is, physical or physiological dependence which is beyond voluntary control; and use of tobacco or nicotine to prevent withdrawal symptoms. Dependency may be influenced by a number of factors, including physical characteristics of the user (e.g., genetic predisposition, age, gender, or weight), personality, or socioeconomic class.

By "treating" is meant the medical management of a patient with the intent that a cure, amelioration, or prevention of a disease, pathological condition, or disorder will result. This term includes active treatment, that is, treatment directed specifically toward improvement of a disease, pathological condition, or disorder, and also includes causal treatment, that is, treatment directed toward removal of the cause of the disease, pathological condition, or disorder. In addition, this term includes palliative treatment, that is, treatment designed for the relief of symptoms rather than the curing of the disease, pathological condition, or disorder; preventive treatment, that is, treatment directed to prevention of the disease, pathological condition, or disorder; and supportive treatment, that is, treatment employed to supplement another specific therapy directed toward the improvement of the disease, pathological condition, or disorder. The term "treating" also includes symptomatic treatment, that is, treatment directed toward constitutional symptoms of the disease, pathological condition, or disorder.

By "suppressing" is meant reducing the desire, need, or number of usages of tobacco or nicotine.

By "therapeutically-effective amount" is meant an amount of a cytidine-containing, cytosine-containing compound, a uridine-containing compound, a creatine-containing compound, an adenosine-containing compound, and an adenosine-elevating compound sufficient to produce a healing, curative, prophylactic, stabilizing, or ameliorative effect in the treatment or suppression of tobacco or nicotine usage or dependence.

By "cytidine-containing compound" is meant any compound that includes, as a component, cytidine, CMP, CDP, CTP, dCMP, dCDP, or dCTP. Cytidine-containing compounds can include analogs of cytidine. Preferred cytidine-containing compounds include, without limitation, CDP-choline and cytidine 5'-diphosphocholine, frequently prepared as cytidine 5'-diphosphocholine [sodium salt] and also known as citicoline.

By "cytosine-containing compound" is meant any compound that includes, as a component, cytosine. Cytosine-containing compounds can include analogs of cytosine.

By "adenosine-containing compound" is meant any compound that includes, as a component, adenosine. Adenosine-containing compounds can include analogs of adenosine.

By "adenosine-elevating compound" is meant any compound that elevates brain adenosine levels, for example, compounds which inhibit or alter adenosine transport or metabolism (e.g., dipyridamole or S-adenosylmethionine).

By "uridine-containing compound" is meant any compound that includes as a component, uridine or UTP. Uridine-containing compounds can include analogs of uridine, for example, triacetyl uridine.

By "creatine-containing compound" is meant any compound that includes as a component, creatine. Creatine-containing compounds can include analogs of creatine.

By "phospholipid" is meant a lipid containing phosphorus, e.g., phosphatidic acids (e.g., lecithin), phosphoglycerides, sphingomyelin, and plasmalogens. By "phospholipid precursor" is meant a substance that is built into a phospholipid during synthesis of the phospholipid, e.g., fatty acids, glycerol, or sphingosine.

By "child or adolescent" is meant an individual who has not attained complete growth and maturity. Generally, a child or adolescent is under twenty-one years of age.

By "older adult" is meant an individual who is in the later stage of life. Generally, an older adult is over sixty years of age.

The compounds utilized herein are relatively non-toxic, and CDP-choline, uridine, and triacetyl uridine, in particular, are pharmocokinetically understood and known to be well tolerated by mammals. The present invention, therefore, provides treatments that are likely to have few adverse effects and may be administered to children and adolescents, as well as the elderly, or those whose health is compromised due to existing physical conditions.

Other features and advantages will be apparent from the following description and the claims.

DETAILED DESCRIPTION OF THE INVENTION

The invention described herein features methods for the treatment or suppression of tobacco or nicotine dependence or usage.

To this end, the invention features the use of cytidine-containing, cytosine-containing, uridine-containing, creatine-containing, adenosine-containing, and adenosine-elevating compounds to alleviate symptoms of these disorders. A preferred cytidine-containing compound is CDP-choline (also referred to as citicoline or CDP choline [sodium salt]), a preferred adenosine-containing compound is S-adenosylmethionine (SAMe), and a preferred uridine-containing compound is triacetyl uridine.

The cytidine-containing, cytosine-containing, uridine-containing, creatine-containing, adenosine-containing, or adenosine-elevating compounds may be co-administered with other compounds that are precursors for the synthesis of brain phospholipids, e.g., fatty acids, lipids, or lecithin.

Tobacco or Nicotine Usage or Dependence

Figure 1:
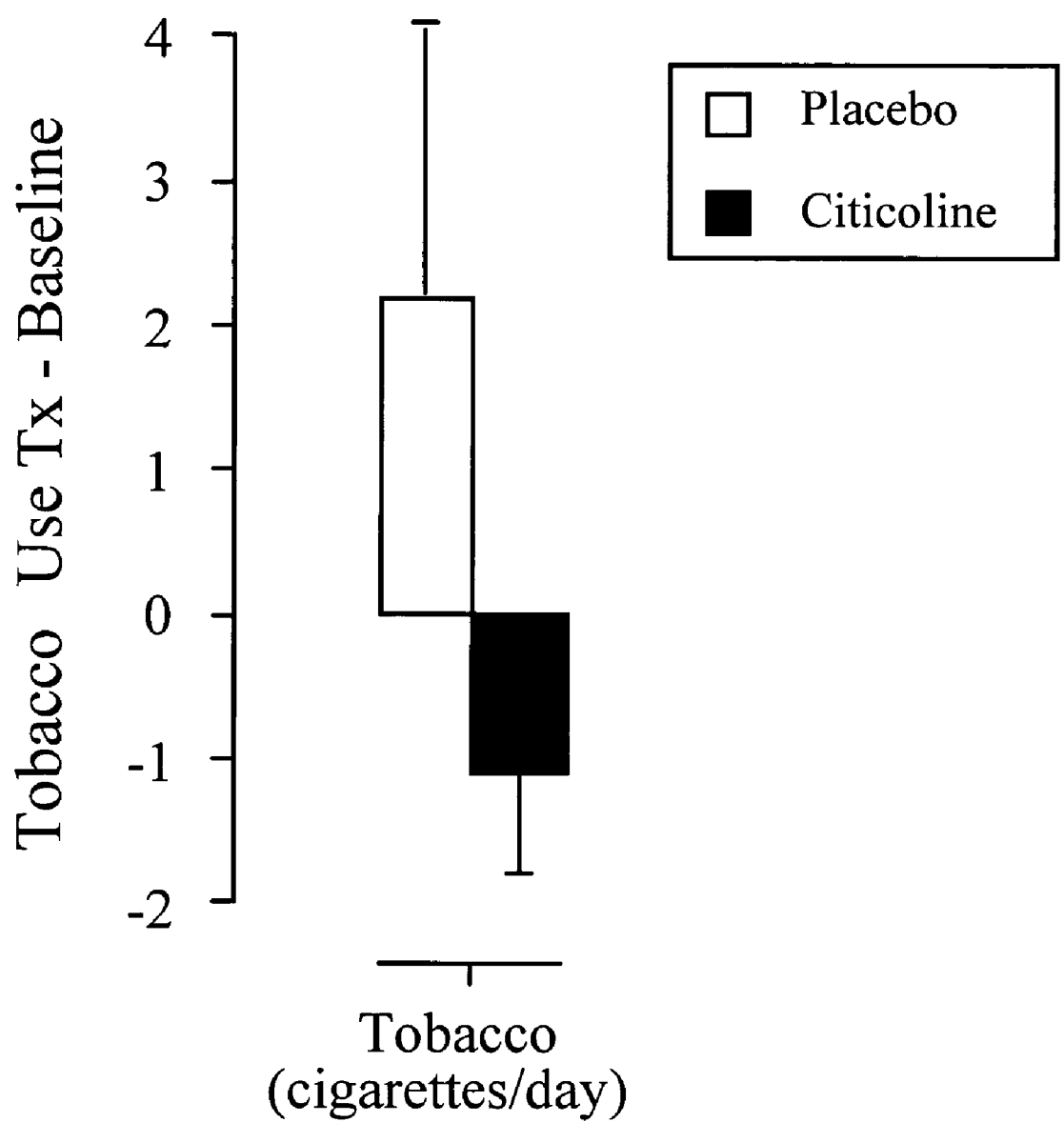
FIG. 1 is a graph of the effects of citicoline on tobacco use.

Surprisingly, we have discovered that CDP-choline is useful for the treatment of tobacco or nicotine dependence or usage, and believe that other, related compounds may be similarly useful. Data in FIG. 1 show that the administration of citicoline reduces the usage of tobacco (expressed as a number of cigarettes smoked per day) compared to usage by human subjects receiving a placebo.

Cytidine-Containing and Cytosine-Containing Compounds

Useful cytidine-containing or cytosine-containing compounds may include any compound comprising one of the following: cytosine, cytidine, CMP, CDP, CTP, dCMP, dCDP, and dCTP. Preferred cytidine-containing compounds include CDP-choline and cytidine 5'-diphosphocholine [sodium salt]. This list of cytidine-containing and cytosine-containing compounds is provided to illustrate, rather than to limit the invention, and the compounds described above are commercially available, for example, from Sigma Chemical Company (St. Louis, Mo.).

Figure 2:
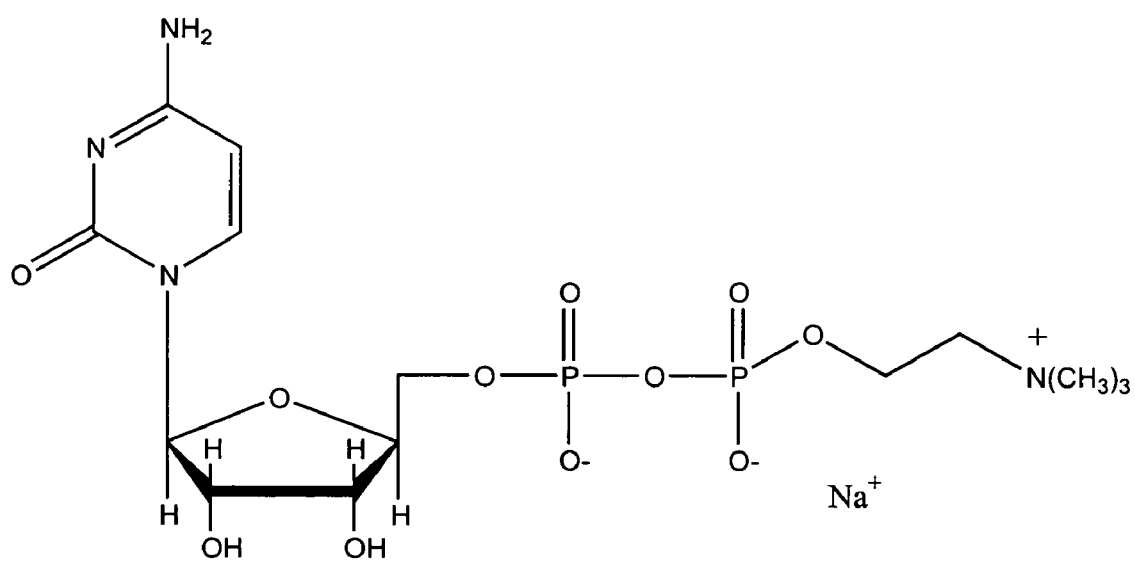
FIG. 2 is a schematic illustration of the molecular structure of CDP-choline.

CDP-choline is a naturally occurring compound that is hydrolyzed into its components of cytidine and choline in vivo. CDP-choline is synthesized from cytidine-5'-triphosphate and phosphocholine with accompanying production of inorganic pyrophosphate in a reversible reaction catalyzed by the enzyme CTP:phosphocholine cytidylyltransferase (Weiss, Life Sciences 56:637–660, 1995). CDP-choline is available for oral administration in a 500 mg oblong tablet. Each tablet contains 522.5 mg CDP-choline sodium, equivalent to 500 mg of CDP-choline. Matching placebo tablets are also available. The excipients contained in both active and placebo tablets are talc, magnesium stearate, colloidal silicon dioxide, hydrogenated castor oil, sodium carboxy-methylcellulose, and microcrystalline cellulose. The molecular structure of CDP-choline [sodium salt] is provided in FIG. 2.

Other formulations for treatment or suppression of tobacco or nicotine usage or dependence may take the form of a cytosine-containing or cytidine-containing compound combined with a pharmaceutically-acceptable diluent, carrier, stabilizer, or excipient.

Adenosine-Containing and Adenosine-Elevating Compounds

Adenosine-containing or adenosine-elevating compounds also provide useful therapies. Useful adenosine-containing or adenosine-elevating compounds include, without limitation, any compound comprising one of the following adenosine, ATP, ADP, or AMP. One preferred adenosine-containing compound is S-adenosylmethionine (SAMe).

In addition, compounds are known that are capable of increasing adenosine levels by other mechanisms. For example, adenosine uptake can be inhibited by a number of known compounds, including propentofylline (described in U.S. Pat. No. 5,919,789). Another known compound that inhibits adenosine uptake is EHNA.

Other useful compounds that can be used to increase brain adenosine levels are those that inhibit enzymes that break down adenosine, (e.g., adenosine deaminase and adenosine kinase). Finally, administering compounds that contain adenosine or precursors of adenosine, which are released as adenosine in vivo, can also be used.

Uridine-Containing Compounds

Uridine and uridine-containing compounds provide useful therapies because these compounds can be converted to CTP, a rate-limiting factor in PC biosynthesis (Wurtman et al., Biochemical Pharmacology 60:989–992, 2000). Useful uridine-containing compounds include, without limitation, any compound comprising uridine, UTP, UDP, or UMP. A preferred uridine-containing compound is triacetyl uridine. Uridine and uridine-containing compounds and analogs are well tolerated in humans.

Creatine-Containing Compounds

Creatine and creatine-containing compounds provide useful therapies because these compounds, by virtue of increasing brain phospholipid levels, can raise the levels of ATP. Creatine and creatine-containing compounds are known to be well tolerated at relatively high doses in humans.

Administration

Conventional pharmaceutical practice is employed to provide suitable formulations or compositions for administration to patients. Oral administration is preferred, but any other appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, or aerosol administration. Therapeutic formulations may be in the form of liquid solutions or suspensions (as, for example, for intravenous administration); for oral administration, formulations may be in the form of liquids, tablets, or capsules; and for intranasal formulations, in the form of powders, nasal drops, or aerosols.

Methods well known in the art for making formulations are described, for example, in "Remington: The Science and Practice of Pharmacy" (20th ed.) ed. A.R. Gennaro, 2000, Lippincott, Philadelphia, Pa. Formulations for parenteral administration may, for example, contain excipients, sterile water, saline, polyalkylene glycols such as polyethylene glycol, oils of vegetable origin, or hydrogenated napthalenes.

If desired, slow release or extended release delivery systems may be utilized. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Preferably, the compounds of the invention, such as CDP-choline, are administered at a dosage of at least 500 mg twice daily by oral administration. Orally administered CDP-choline is bioavailable, with more than 99% of CDP-choline and/or its metabolites absorbed and less than 1% excreted in feces. CDP-choline, administered either orally or intravenously, is rapidly converted into the two major circulating metabolites, choline and cytidine. Major excretion routes are lung (12.9%) and urine (2.4%); the rest of the dose (83.9%) is apparently metabolized and retained in tissues.

In general, the compounds of the invention, such as CDP-choline, uridine, UTP, creatine, or SAMe, are administered at a dosage appropriate to the effect to be achieved and are typically administered in unit dosage form. The dosage preferably ranges from 50 mg per day to 2000 mg per day. The exact dosage of the compound may be dependent, for example, upon the age and weight of the recipient, the route of administration, and the severity and nature of the symptoms to be treated. In general, the dosage selected should be sufficient to treat or suppress tobacco or nicotine usage or dependence, or one or more symptoms thereof, without producing significant toxic or undesirable side effects. As noted above, the preferred route of administration for most indications is oral.

In the case of CDP-choline, there have been no reported cases of overdoses. CDP-choline toxicity is largely self-limiting, ingestion of large amounts in preclinical studies shows common cholinergic symptoms (salivation, lacrimation, urination, defecation, and vomiting).

Combination with Other Therapeutics

The cytidine-containing, cytosine-containing, uridine-containing, creatine-containing, adenosine-containing, and adenosine-elevating compounds of the invention may be administered as a monotherapy, in combination with each other, or in combination with other compounds for the treatment of substance abuse disorders, including compounds for the treatment or suppression of tobacco or nicotine usage or dependence, or other associated physiological or psychological conditions.

The compounds of the invention, may be administered in conjunction with lower doses of current treatments for these disorders, including stimulants and antidepressants. For example, the compounds of the invention may be administered with phospholipids, e.g., lecithin, or with brain phospholipid precursors, e.g., fatty acids or lipids, or may be administered as an adjunct to standard therapy for the treatment of substance abuse disorders.

In one particular example, the compound of the invention may be administered in combination with an antidepressant, anticonvulsant, antianxiety, antimanic, antipyschotic, antiobsessional, sedative-hypnotic, stimulant, or anti-hypertensive medication. Examples of these medications include, but are not limited to, the antianxiety medications, alprazolam, buspirone hydrochloride, chlordiazepoxide, chlordiazepoxide hydrochloride, clorazepate dipotassium, desipramine hydrochloride, diazepam, halazepam, hydroxyzine hydrochloride, hydroxyzine pamoate, lorazepam, meprobamate, oxazepam, prazepam, prochlorperazine maleate, prochlorperazine, prochlorperazine edisylate, and trimipramine maleate; the anticonvulsants, amobarbital, amobarbital sodium, carbamazepine, chlordiazepoxide, chlordiazepoxide hydrochloride, clorazepate dipotassium, diazepam, divalproex sodium, ethosuximide, ethotoin, gabapentin, lamotrigine, magnesium sulfate, mephenytoin, mephobarbital, methsuximide, paramethadione, pentobarbital sodium, phenacemide, phenobarbital, phenobarbital sodium, phensuximide, phenytoin, phenytoin sodium, primidone, secobarbital sodium, trimethadione, valproic acid, and clonazepam; the antidepressants, amitriptyline hydrochloride, amoxapine, bupropion hydrochloride, clomipramine hydrochloride, desipramine hydrochloride, doxepin hydrochloride, fluoxetine, fluvoxamine, imipramine hydrochloride, imipramine pamoate, isocarboxazid, lamotrigine, maprotoline hydrochloride, nortriptyline hydrochloride, paroxetine hydrochloride, phenelzine sulfate, protriptyline hydrochloride, sertraline hydrochloride, tranylcypromine sulfate, trazodone hydrochloride, trimipramine maleate, and venlafaxine hydrochloride; the antimanic medications, lithium carbonate and lithium citrate; the antiobsessional medications, fluvoxamine, and clomipramine hydrochloride; the antipsychotic medications, acetophenazine maleate, chlorpromazine hydrochloride, chlorprothixene, chlorprothixene hydrochloride, clozapine, fluphenazine decanoate, fluphenazine enathrate, fluphenazine hydrochloride, haloperidol decanoate, haloperidol, haloperidol lactate, lithium carbonate, lithium citrate, loxapine hydrochloride, loxapine succinate, mesoridazine besylate, molindone hydrochloride, perphenazine, pimozide, prochlorperazine maleate, prochlorperazine, prochlorperazine edisylate, promazine hydrochloride, risperidone, thioridazine, thioridazine hydrochloride, thiothixene, thiothixene hydrochloride, and trifluoperzine hydrochloride; the sedative-hypnotic medications, amobarbital, amobarbital sodium, aprobarbital, butabarbital, chloral hydrate, chlordiazepoxide, chlordiazepoxide hydrochloride, clorazepate dipotassium, diazepam, diphenhydramine, estazolam, ethchlorvynol, flurazepam hydrochloride, glutethimide, hydroxyzine hydrochloride, hydroxyzine pamoate, lorazepam, methotrimeprazine hydrochloride, midazolam hydrochloride, non prescription, oxazepam, pentobarbital sodium, phenobarbital, phenobarbital sodium, quazepam, secobarbital sodium, temazepam, triazolam, and zolpidem tartrate; the stimulants, dextroamphetamine sulfate, methamphetamine hydrochloride, methylphenidate hydrochloride, and pemoline; and the anti-hypertensive, clonidine.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

The invention claimed is:

1. A method of treating or suppressing tobacco or nicotine dependence or usage, said method comprising administering to a human in need thereof a therapeutically-effective amount of a cytidine-containing compound further comprising choline.

2. The method of claim 1, wherein said cytidine-containing compound is CDP-choline.

3. The method of claim 2, wherein said CDP-choline is administered orally.

4. The method of claim 1, wherein said administering is chronic.

5. The method of claim 1, wherein said human is a child or adolescent.

6. The method of claim 1, wherein said human is an older adult.

* * * * *

UNITED STATES PATENT AND TRADEMARK OFFICE
CERTIFICATE OF CORRECTION

PATENT NO. : 7,053,064 B2
APPLICATION NO. : 10/703695
DATED : May 30, 2006
INVENTOR(S) : Lukas It is certified that error appears in the above-identified patent and that said Letters Patent is hereby corrected as shown below:

Column 3, Line 30, replace "pharmocokinetically" with --pharmacokinetically--.

Column 5, Lines 34-35, replace "napthalenes" with --naphthalenes--.

Column 6,
    Line 32, replace "antipyschotic" with --antipsychotic--;
    Lines 55-56, replace "maprotoline" with --maprotiline--; and
    Line 66, replace "enathrate" with --enanthate--.

Column 7, Lines 6-7, replace "trifluoperzine" with --trifluoperazine--.

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,053,064 B2 |
| APPLICATION NO. | : 10/703695 |
| DATED | : May 30, 2006 |
| INVENTOR(S) | : Scott Lukas |

It is certified that error appears in the above-identified patent and that said Letters Patent is hereby corrected as shown below:

In the Specifications:

At Column 1, Line 11, following the CROSS REFERENCE TO RELATED APPLICATIONS section, please insert the following section:

--STATEMENT REGARDING FEDERALLY SPONSORED RESEARCH

This invention was made with Government support under Grant No. DA011098 awarded by the National Institutes of Health. The Government has certain rights in the invention.--

Signed and Sealed this
Twenty-sixth Day of February, 2013

Teresa Stanek Rea
*Acting Director of the United States Patent and Trademark Office*